US00PP11325P

United States Patent [19]

Nielsen

[11] Patent Number: Plant 11,325

[45] Date of Patent: Apr. 4, 2000

[54] FICUS PLANT NAMED 'LAUREN'S DELIGHT'

[76] Inventor: Svend Nielsen, Naarupvej 38, DK-5690 Tommerup, Denmark

[21] Appl. No.: 08/953,671

[22] Filed: Oct. 17, 1997

[51] Int. Cl.[7] ..... A01H 5/00

[52] U.S. Cl. ..... Plt./211

[58] Field of Search ..... Plt./88.9, 211

[56] References Cited

U.S. PATENT DOCUMENTS

P.P. 9,856 4/1997 van Geest ..... Plt./88.9

OTHER PUBLICATIONS

The New Royal Horticultural Society Dictionary of Gardening, Ed–in–Chief Anthony Huxley, The Stockton Press, New York, pp. 294–305, 1992.

Peter Walton, Principles and Practices of Plant Science. Prentice Hall, New Jersey, 1988.

UPOV–ROM 1998/01, Plant Variety Database, GTI Jouve Retrieval Software, citation for, 'Ninet', Mar. 16, 1996.

A.B. Graf. Tropica Color Cyclopedia of Exotic Plants and Trees from the Tropics and Syubtropics. Roehrs Company (publishers). New Jersey. p 649, 1978.

*Primary Examiner*—Howard J. Locker
*Assistant Examiner*—Anne Marie Grünberg
*Attorney, Agent, or Firm*—William M. Hobby, III

[57] ABSTRACT

A new and distinct cultivar of *Ficus benjamina* called 'Lauren's Delight' is characterized by a distinct variegated foliage that displays irregular cream-colored margins and two shades of green, occurring in asymmetric shapes and sizes, in the central area of the leaf. Slight differences in leaf shape and variegation pattern between leaves add to the visual appearance of the plant. The plant is also characterized by small leaves averaging approximately 4.5 cm in length and 1.5 cm in width. A freely branching growth habit gives the plant a full and compact appearance.

2 Drawing Sheets

SUMMARY OF THE INVENTION

A new and distinct cultivar of *Ficus benjamina* called 'Lauren's Delight' characterized by a distinct variegated foliage that displays irregular cream-colored margins and two shades of green, occurring in asymmetric shapes and sizes, in the central area of the leaf. Slight differences in leaf shape and variegation pattern between leaves add to the visual appearance of the plant. The plant is also characterized by small leaves averaging approximately 4.5 cm in length and 1.5 cm in width. A freely branching growth habit gives the plant a full and compact appearance.

BRIEF DESCRIPTION OF THE DRAWINGS

The accompanying color photographs show typical specimens of the plant and leaves of the new variety.

DETAILED DESCRIPTION OF THE NEW VARIETY

Figure 1:
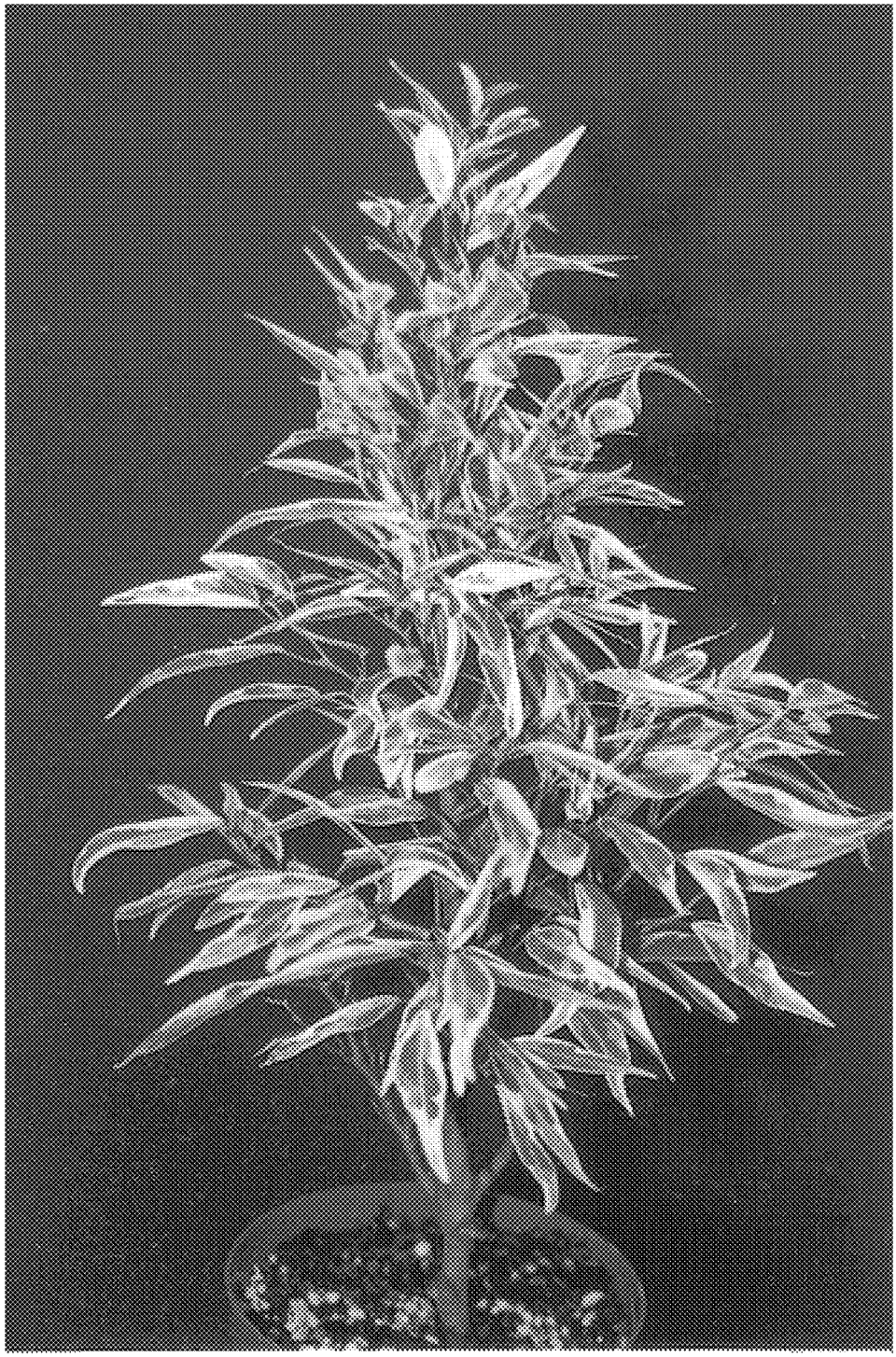
FIG. 1 is a color photograph of the present Ficus plant in a 12 cm pot.
Figure 2:
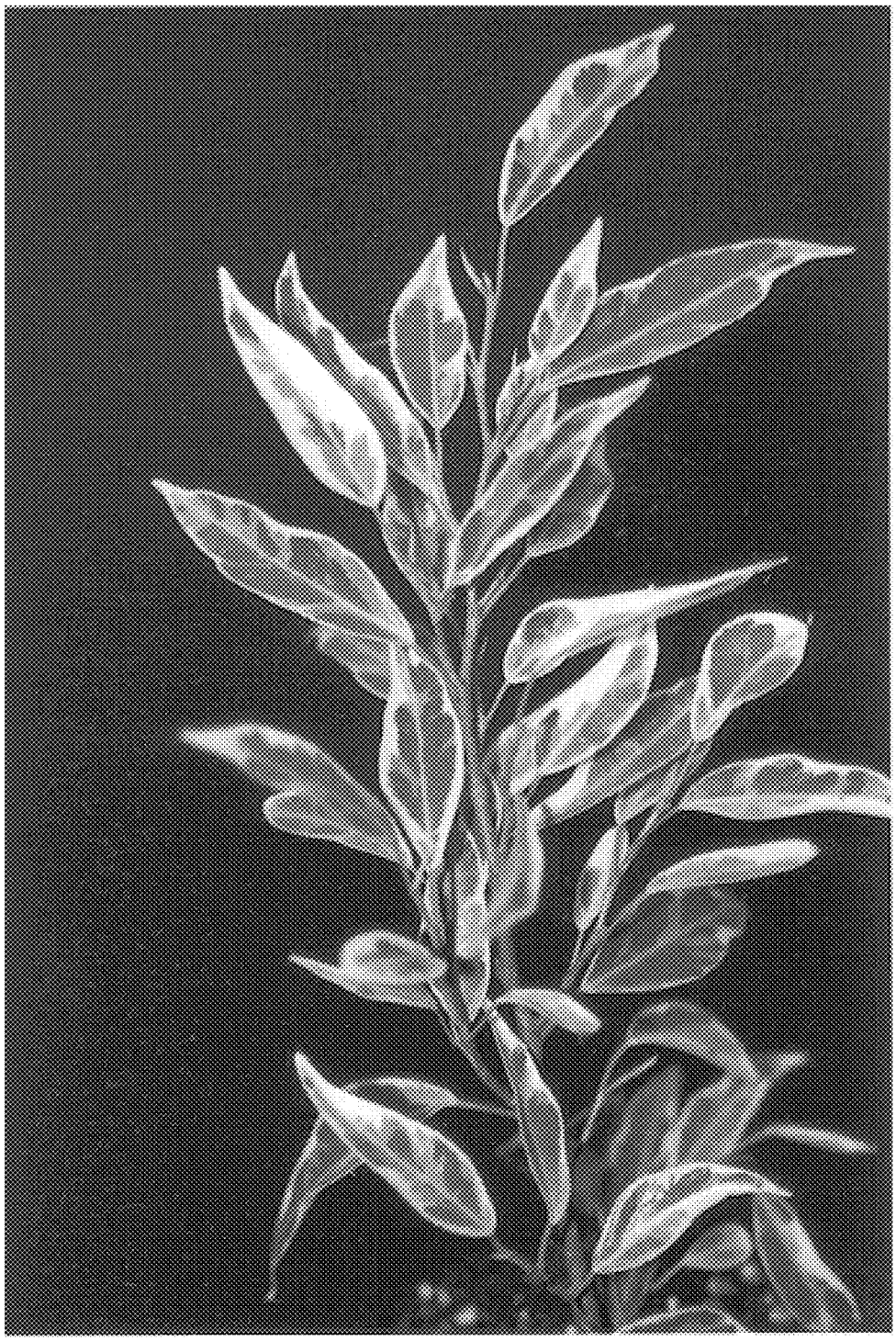
FIG. 2 is a color photograph of a single stem of the present Ficus plant showing leaf shape and coloration.

The present invention relates to a new distinct cultivar of a *Ficus benjamina* plant. All color references are based on The R.H.S. Colour Chart, 1996, by The Royal Horticultural Society, London, England. All Colors are approximate since color varies with horticultural practices, such as light level and fertilization rate. This Cultivar originated and was asexually propagated in the Inventor's Nursery in Tommerup, Denmark.

Parentage: a cultivar of *Ficus benjamina*. In 1988 the Inventor discovered a small leaved mutation in a *Ficus benjamina* 'Exotica' plant in his nursery. This mutation was developed through cuttings into a Ficus plant called 'NATASCHA' (not patented in the US). 'NATASHA' was grown in the Inventor's Nursery in Tommerup, Denmark, where he discovered a single predominately white leaved mutation among the plants in the cultivated area of the nursery. This mutation was tissue cultured and the tissue cultured plants were radiated to obtain new mutations which were test grown and selected over a period of several years. A new and distinct cultivar of *Ficus benjamina* called 'Lauren's Delight' originated as single plant. 'Lauren's Delight' is asexually propagated by tip and joint cuttings rooted under mist propagation.

Leaf color: The Surface of the leaves displayed three basic colors. The Cream-colored outer edge of the leaves is R.H.S. 157A. This edge extends around the entire leaf blade and is visible on both the top and bottom of the leaf surfaces. The width of the cream-colored margin is variable and in a few leaves it extends in as far as the leaf midrib. The central portion of the leaf consists of two different colors of green. The darker green area is R.H.S. 147A and the lighter green area is R.H.S. 189A. Both green colors occur in patches of irregular size and shape that are adjacent to each other and give an overall mottled effect. In most leaves, the darker green patches cover more of the leaf surface than the lighter areas, although in a few leaves, the opposite is true. When looking at the whole plant, differences in individual leaf coloration are not significant compared to the overall pleasing effect of the tricolored leaves. The underside or bottom of the leaves displays three basic colors. The outer edge is again a cream, R.H.S. 157A, and generally mirrors the pattern seen on the upper leaf surface. There are also non-uniform areas of green in two shades on the underside of the leaf. The darker areas are R.H.S. 147A and the lighter areas are R.H.S. 147B. In contrast to the cream-colored areas, the green areas on the underside of the leaves do not correspond to the same green colors on the surface.

Leaf size and shape: Leaf measurements were taken of typical leaves and average leaf width is 1.5±0.4 cm and average leaf length is 4.5±0.8 cm. Average length to width ratio of leaves is 3.0±0.5. The general overall leaf shape is lanceolate. Leaf margins are entire, leaf tips are acuminate and leaf bases are obtuse. There is, however, some variation in leaf shape but the majority of leaves conform to this overall leaf shape.

Petiole: The Petiole color is R.H.S. 144A and the Petiole length averages 1±0.2 cm.

Stem: The Stem color is R.H.S. 199B/C. The plant branches freely, producing up to 18 or more lateral offshoots per 30 cm length of main stem. Each lateral shoot also develops secondary shoots as it matures. In a 13 cm standard pot, after approximately 24 weeks of growth under appropriate conditions beginning with tip and joint cuttings, rooted under mist propagation 'Lauren's Delight' reaches approximately 23 cm in height from the solid surface to the apical growing point and 23 cm in width. The ultimate size of 'Lauren's Delight' if planted in a larger container and grown under appropriate conditions is not known.

Flowers and fruit: To date, flowering and fruiting have not been observed in 'Lauren's Delight'. Flowering and Fruiting are expected to be similar to *Ficus benjamina* which would not occur until approximately ten years after initial creation of the plant.

I claim:

1. A new and distinct cultivar of Ficus plant called 'Lauren's Delight', substantially as herein illustrated and described, characterized by variegated foliage of irregular cream-colored margins and two shades of green occurring in asymmetric shapes and sizes in the central area of the leaf blade and having slight differences in leaf shape and variegation pattern.

* * * * *